Figure 1A:
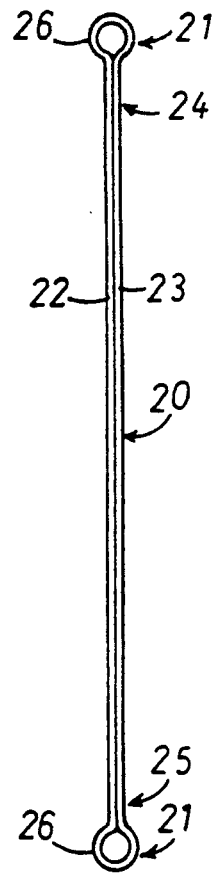

United States Patent [19]

Mehdian

[11] Patent Number: 5,092,868
[45] Date of Patent: Mar. 3, 1992

[54] APPARATUS FOR USE IN THE TREATMENT OF SPINAL DISORDERS

[76] Inventor: Seyed M. H. Mehdian, 20 Attwyll Avenue, Heavitree Road, Exeter, Devon, England

[21] Appl. No.: 608,750

[22] Filed: Nov. 5, 1990

Related U.S. Application Data

[63] Continuation of Ser. No. 219,389, Jul. 15, 1988, abandoned.

[30] Foreign Application Priority Data

Jul. 17, 1987 [GB] United Kingdom ............... 8716925

[51] Int. Cl.⁵ .............................................. A61F 5/04
[52] U.S. Cl. .................................................. 606/74
[58] Field of Search ............... 606/74, 91, 103, 72, 606/73; 248/302, 303; 24/17 B, 546, 578, 678; 128/69

[56] References Cited

U.S. PATENT DOCUMENTS

| | | | |
|---|---|---|---|
| 2,802,467 | 8/1957 | McNally | 606/103 |
| 4,557,259 | 12/1985 | Wu | 606/73 |
| 4,570,618 | 2/1986 | Wu | 606/61 |
| 4,643,178 | 2/1987 | Nastari et al. | 606/74 |
| 4,686,970 | 8/1987 | Dove et al. | 128/69 |
| 4,966,600 | 10/1990 | Songer et al. | 606/74 |

OTHER PUBLICATIONS

Zentralblatt für Chirugie; 1933; Nr. 17; Über Einen Neuen Drahtbinder; Dr. Schürch.

Primary Examiner—C. Fred Rosenbaum
Assistant Examiner—William W. Lewis
Attorney, Agent, or Firm—William E. Mouzavires

[57] ABSTRACT

A tie member for insertion through a segment of a spinal column for clamping that segment to a link or frame embracing that segment comprises an endless loop of wire flattened to form two strands substantially parallel and contiguous with one another at least in their end regions in which one strand runs into the other in an end loop. Such a tie member of finite length with the end loops can be readily inserted through a segment of a spinal column, manipulated into and retained in a desired position and have its ends twisted together for clamping. The endless loops obviates any sharp ends that could accidentally cause damage to the spinal column. Ancilliary instruments for use with the tie members include a keeper with arms defining an end recess across which extends a pin on which the tie member end loops can be received, and a twister with a crank handle and a tapered T-shaped groove to receive a keeper, and a puller having a T-shaped handle and a hook compatible with the tie member end loops.

13 Claims, 5 Drawing Sheets

U.S. Patent    Mar. 3, 1992    Sheet 1 of 5    5,092,868

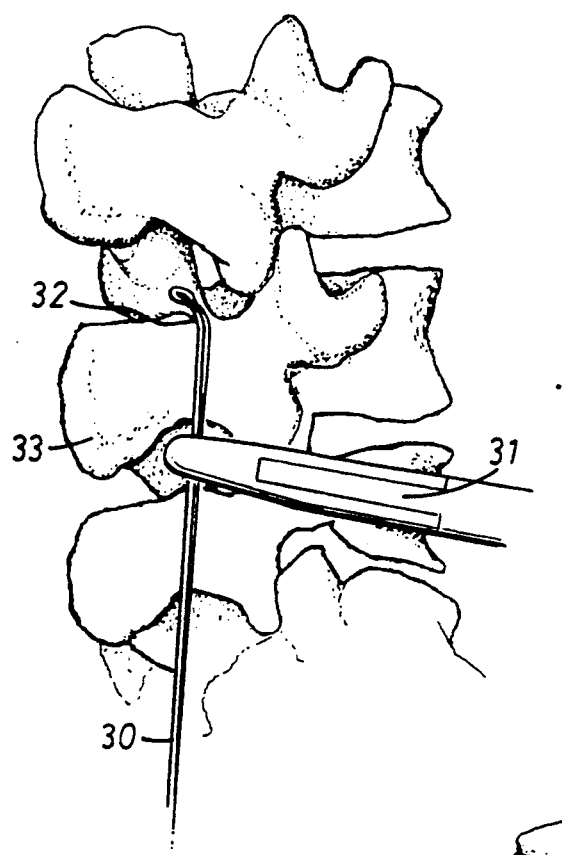
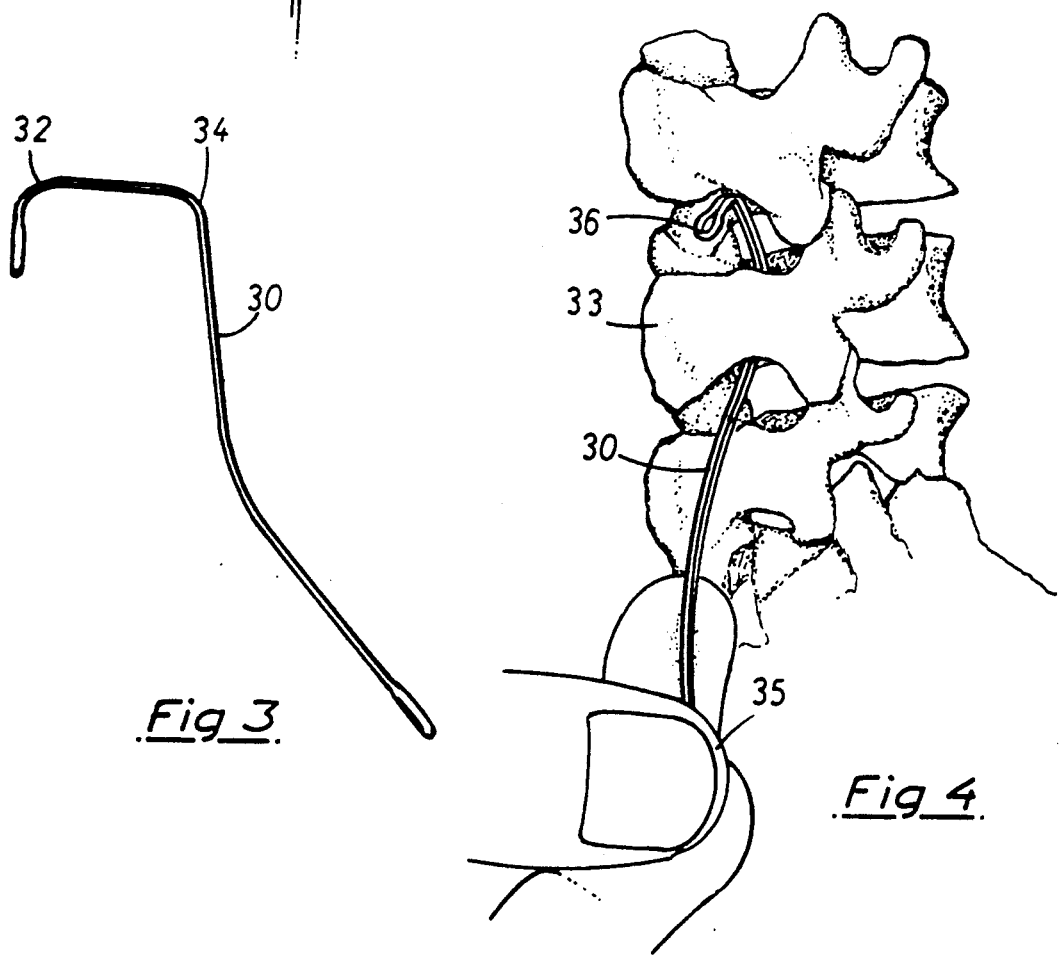

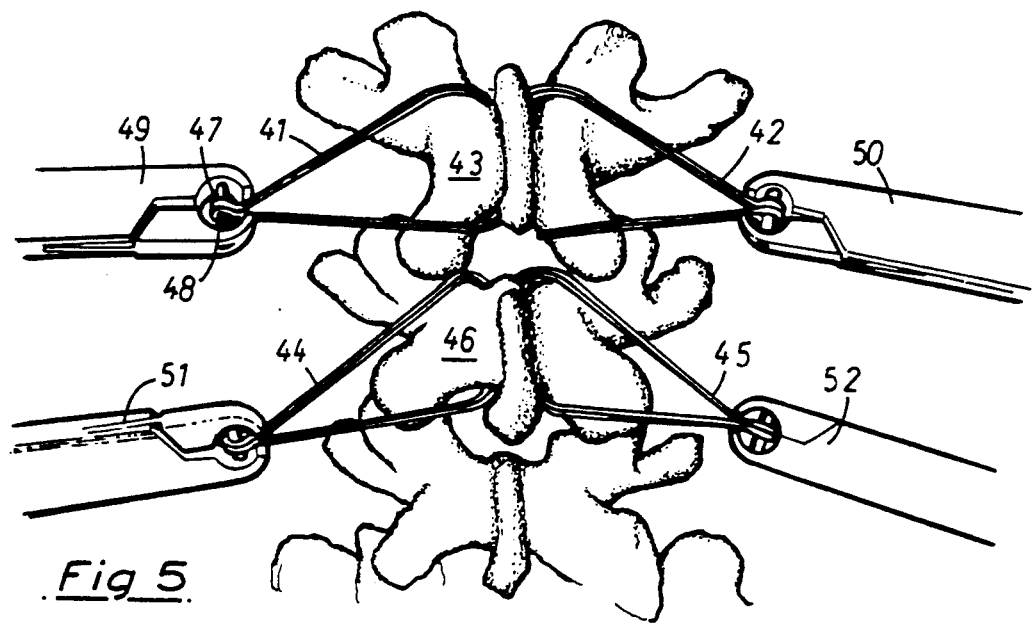
Fig_5.
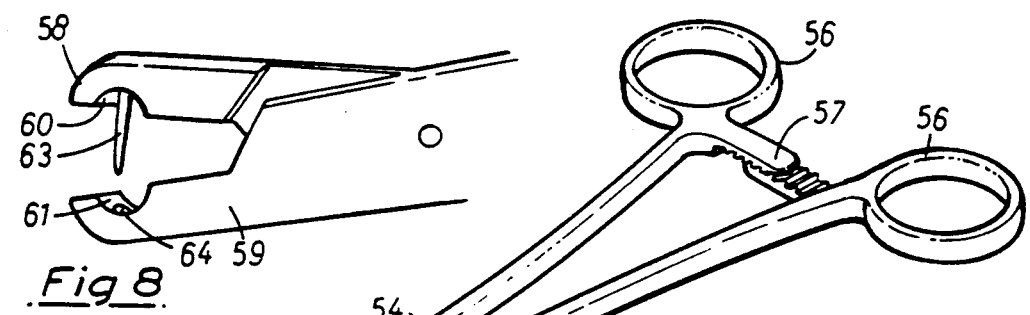
Fig_8.    Fig_6.
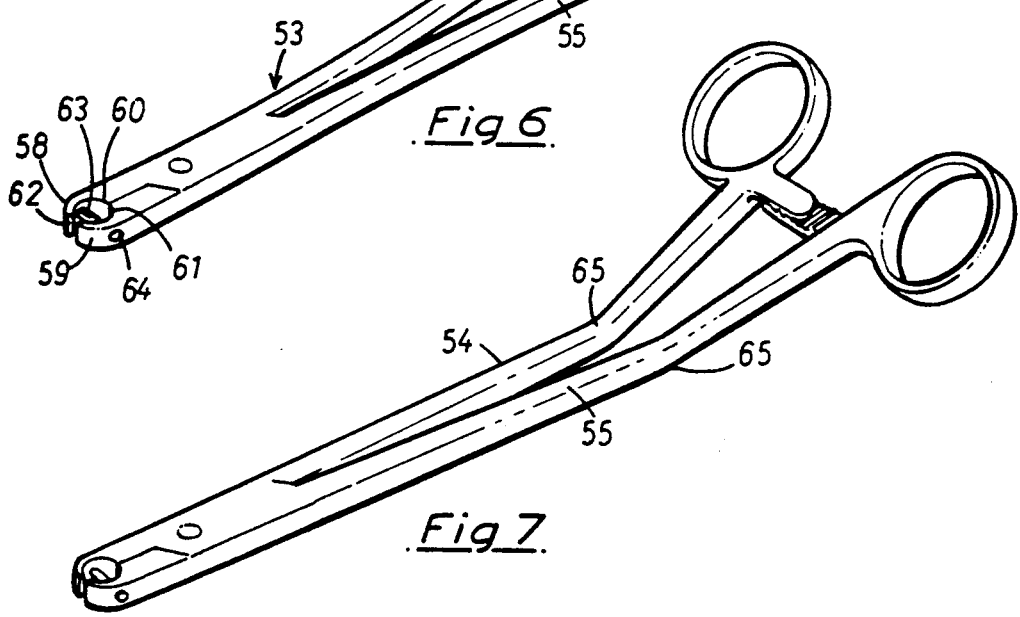
Fig_7.

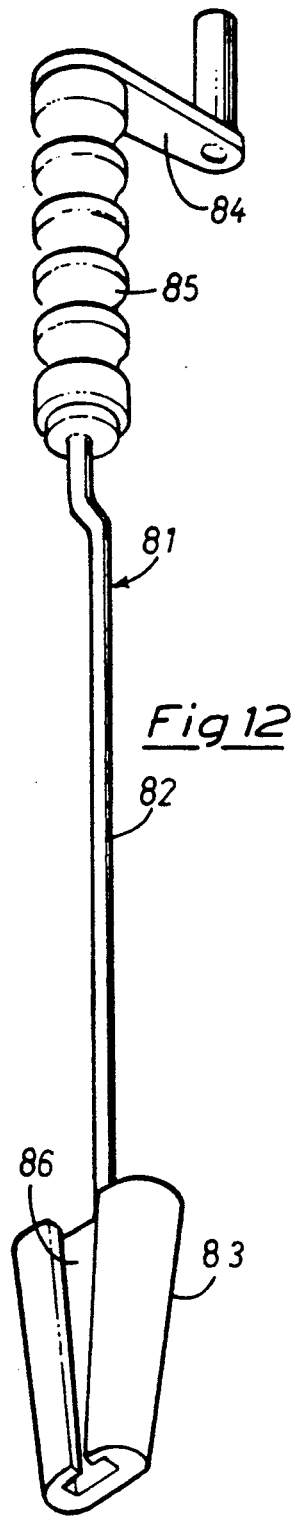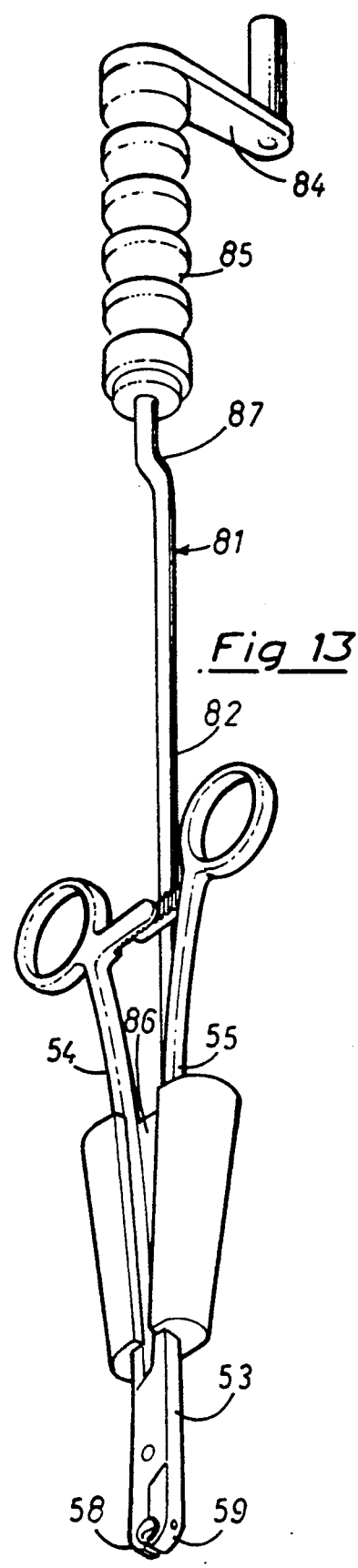

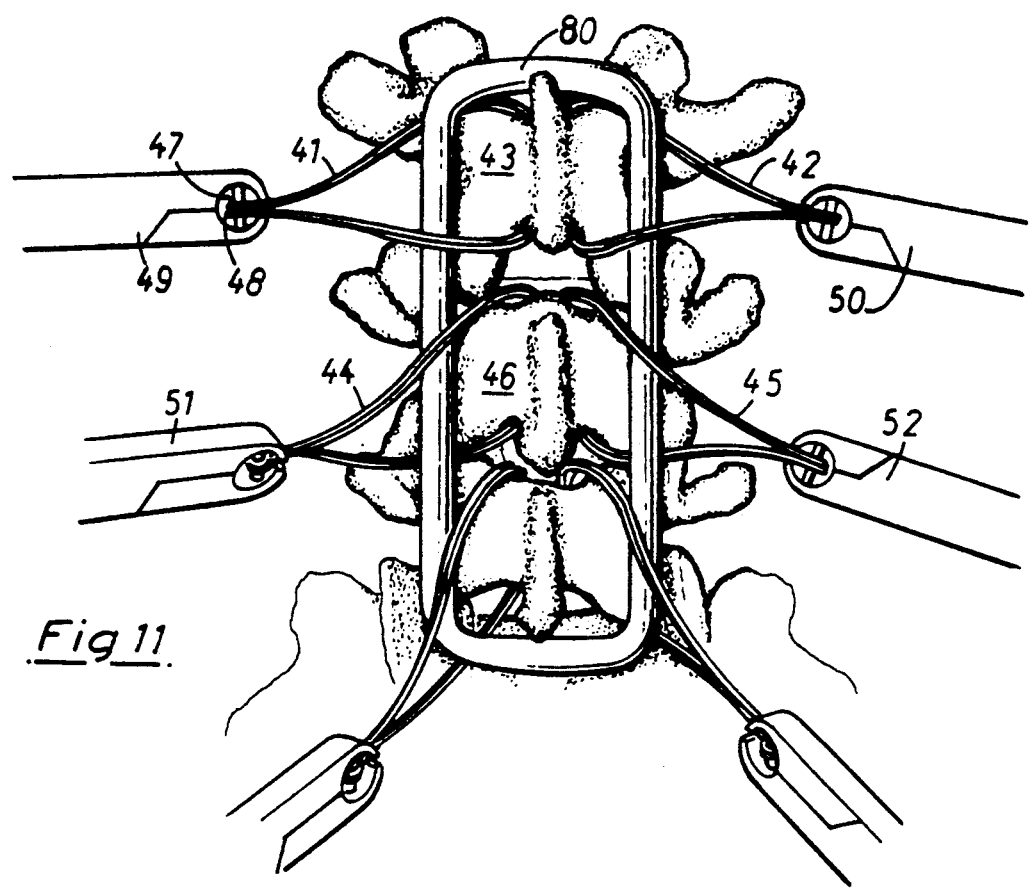
Fig 11.
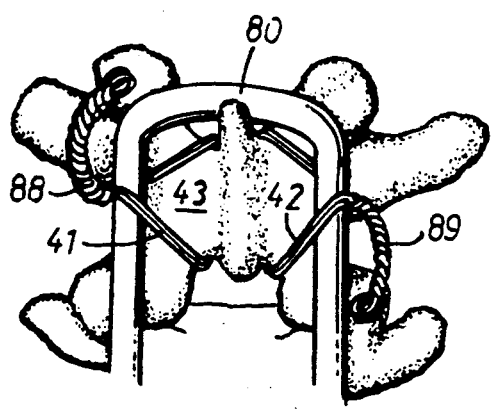
Fig 14.
Fig 15.
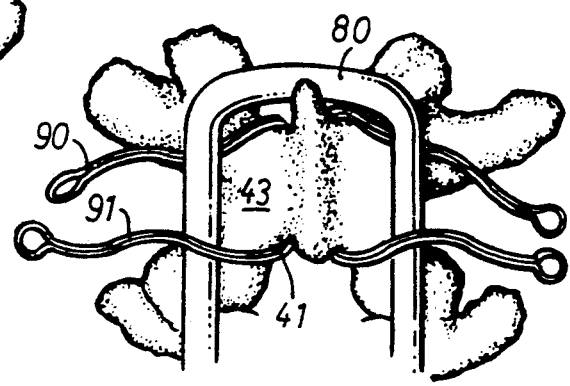

APPARATUS FOR USE IN THE TREATMENT OF SPINAL DISORDERS

RELATED APPLICATION

This is a continuation of my prior co-pending application, Ser. No. 07/219,389 filed July 15, 1988, now abandoned.

DESCRIPTION

The present invention relates to apparatus for use in the treatment of spinal disorders.

In certain methods of treatment of spinal disorders it is desirable to restrict the movement of some segments of the spinal column or to correct the positions of certain segments of the spinal column. In many cases this is done by placing a link or frame round the rear parts of relevant segments of the spinal column and attaching each of the segments concerned to the opposite sides of the link or frame by means of wire tires which are inserted through the centre regions of the segments of the spinal column, the ends of each wire ties being twisted together around the link or frame thereby to secure each of the relevant members of the spinal column to the link or frame. The link or frame may be a ring generally rectangular in shape and the long dimension of the ring may be relatively small so that the ring only encompasses a small number of segments, say three or four, or may be of some considerable length so as to encompass a larger number of segments; alternatively, a pair of L-shaped rods may be used, one on each side of the spinal column, such rods having the advantage by virtue of their length of not being restricted to a predetermined number of segments of the spinal column, though having the disadvantage of permitting some twisting of the spinal column.

When at a subsequent stage of treatment it is desired to disconnect some or all of the relevant segments of the spinal column from the link or frame, it has been common practice hitherto to release each of the ties and, after removing the link or frame, to withdraw each of the wire ties from the spinal column. The release of a wire tie may be effected either by solely untwisting the ends, or by untwisting and then cutting at least one end, or solely by cutting, but which ever procedure is adopted, the withdrawal of a wire tie presents a serious risk to the spinal cord, which could result in paralysis. This risk arises because at least one end of a wire tie is rough, rugged, or sharp and there is a serious risk that such end, when a wire tie is withdrawn from a segment of the spinal column, may, however carefully and gently it is withdrawn, engage and damage the spinal cord.

According to the present invention a tie member for insertion through a segment of a spinal column for clamping that segment to a link or frame embracing that segment comprises an endless loop of wire which is flattened to form two strands extending substantially parallel to one other from one end region to the other end region and substantially contiguous with one another at least adjacent their end regions in each of which one strand runs into the other strand and defines an end loop.

The end loops of a tie member can be substantially circular or can be elongated that is to say elliptical or oval or with substantially parallel sides joined by a substantially circular end portion. Each tie member can have similar shaped end loops at both ends or can have differently shaped loops at opposite ends; thus a tie member can have a substantially circular loop at one end and a rectangular loop at the other end, or yet again can have substantially rectangular loops at both ends.

Preferably the internal diameter of an end loop or the smaller transverse axis internal dimension of an end loop is approximately equal to or is not less than twice the diameter of a strand of the tie member. Whilst the length of a tie member is to a large extent determined by the task which it is required to perform, the length is preferably not less than 75 mm and preferably is not more than 150 mm. It is believed that most requirements can be met by a range of tie members of predetermined lengths of for example 75 mm, 100 mm and 120 mm. The tie members are preferably made of stainless steel.

A tie member embodying the present invention can substantially reduce or obviate the risk and disadvantages mentioned above. Amongst the advantages achieved by a tie member embodying the present invention are that the tie member can at all times have a smooth exterior surface.

A tie member embodying the present invention can be readily bent to a suitable shape prior to insertion into a segment of the spinal column and its entry is greatly eased by the leading end loop. Moreover, the leading end loop can be readily engaged by a puller or keeper which can then be used to pull the tie member through the segment; moreover, the keeper can be used to hold one or both ends of a tie member in any desired position such as not to impede the insertion of further tie members through adjacent or succeeding segments of the spinal column. After all the required tie members have been inserted through selected segments of the spinal column at least one end of each tie member can be released from a keeper to permit insertion of a link or frame to embrace the segments concerned, and thereafter both ends of each tie member can be engaged once more by a single keeper which can then be used to twist the end portions of the tie member together to clamp a segment of the spinal column to the link or frame.

A particular advantage of a tie member embodying the present invention lies in the fact that when, at a later stage in treatment, a tie member is to be withdrawn, it is no longer necessary to cut a tie member, but rather the two end loops of the tie member can be engaged in a keeper which can then be used to untwist the two end portions whereupon the end portions can be separated from one another and each or either end loop engaged by a keeper or puller and gently withdrawn through and from the segment of the spinal column, the smooth exterior surface of the trailing end loop facilitating the passage of the trailing end portion of the tie member into, through and out of the spinal column with greatly reduced risk of damage to the spinal cord passing therethrough.

In order that a tie member embodying the present invention may be used to best advantage ancilliary instruments are desirable for use therewith. Such instruments comprises for example a tie member puller, one or more tie member keepers such as a straight keeper, a curved keeper, or a flexible weighted keeper, and a twister to enable the end portions of the or each wire tie to be twisted together and/or untwisted. A further aspect of the present invention lies in such ancilliary instruments as herein described and useful for utilising tie members to their best advantage.

Figure 1B:
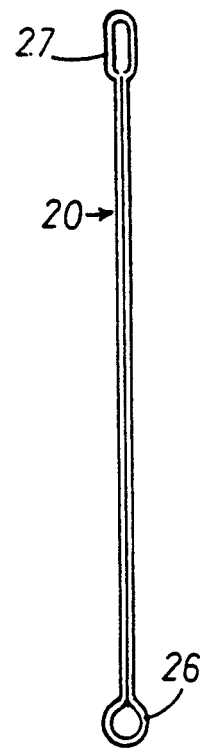
Figure 1C:
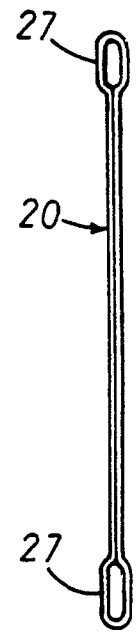
Figure 9:
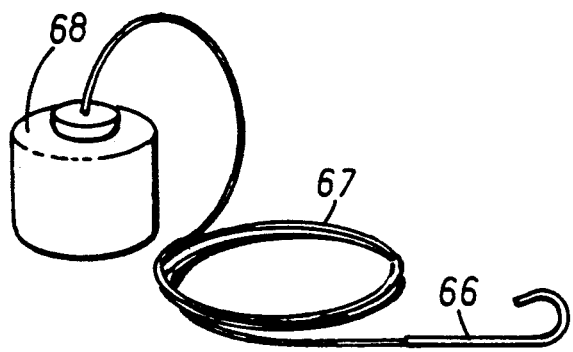
Figure 10:
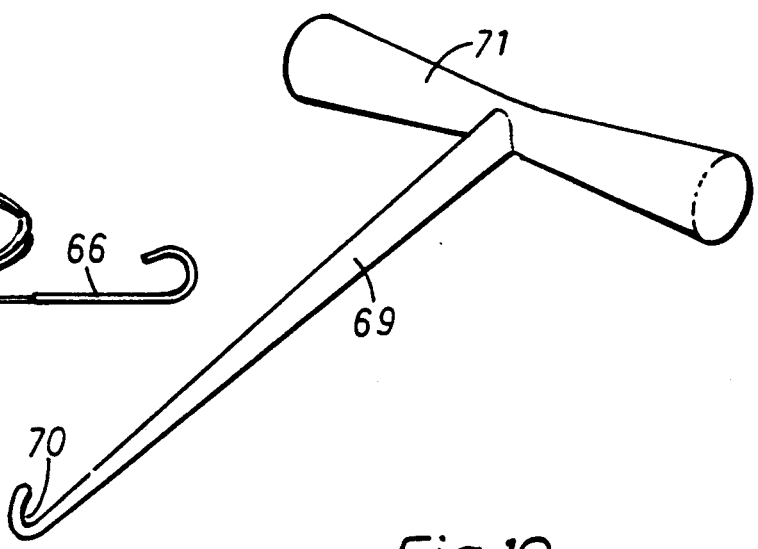

The invention will be further described by way of example with reference to the accompanying drawings, in which:

FIGS. 1A, 1B and 1C are plan views of various length tie members,

FIG. 2 is a diagrammatic perspective view illustrating a preparatory stage, prior to the insertion of a tie member through a segment of a spinal column, FIG. 3 is an illustration of a tie member suitably shaped prior to its insertion through a segment of the spinal column, FIG. 4 is a diagrammatic perspective view illustrating the insertion of the tie member of FIG. 3 through a segment of the spinal column, FIG. 5 is a diagrammatic perspective view showing four tie members after insertion through opposite sides of adjacent segments of the spinal column, FIG. 6 is a perspective view of one form of tie member keeper, FIG. 7 is a perspective view of another form of tie member keeper, FIG. 8 is a detail view to a larger scale of the tie member engaging portion of the keeper or FIG. 6 and/or FIG. 7, FIG. 9 is a diagrammatic perspective illustration of a further form of keeper, FIG. 10 is a perspective illustration of an insert puller, FIG. 11 is a diagrammatic perspective view showing six tie members inserted through three segments of a spinal column, such segments being embraced by a link or frame, and the end loops of the tie members engaged by keepers, FIG. 12 is a perspective view of a twister, FIG. 13 is a perspective view illustrating the engagement of the twister of FIG. 12 with a keeper such as the keeper of FIG. 6, FIG. 14 is a diagrammatic perspective illustration showing two tie members with their end portions twisted together to clamp a segment of the spinal column to the opposite sides of a link or frame, and FIG. 15 is a diagrammatic perspective illustration showing, at a subsequent stage of treatment, the end portions of two wire ties, after being untwisted preparatory to withdrawal from a segment of the spinal column.

Referring first to FIG. 1, a tie member 20 for insertion through a segment of the spinal column comprises a flattened wire loop having an end loop 21 at each end. The flattened loop has two strands 22, 23 which extend substantially parallel to one another from end region 24 to the other end region 25. The two strands 22, 23, are substantially contiguous with one another at least adjacent their end regions 24, 25 in each of which one strand, such as 22, runs into the other strand 23 in an end loop 21. The end loops 21 may be substantially circular as illustrated in FIG. 1A as illustrated at 26 but can equally well be elliptical or oval. Another form of end loop is illustrated in FIG. 1B at 27 and is substantially rectangular with spaced parallel sides joined by a substantially circular end. A tie member can have substantially the same end loop at both ends such as illustrated in FIG. 1A or in FIG. 1C or can have a circular end loop 26 at one end and an elongated rectangular loop 27 at the other end as illustrated in FIG. 1B. The tie members need not all have the same length and for most purposes it is believed that three lengths of tie member will suffice, such as illustrated in FIG. 1A, FIG. 1B and FIG. 1C. Suitable lengths are from 75 mm to 150 mm.

The tie members are preferably made of stainless steel. The transverse internal dimension of an end loop, that is to say the internal diameter of a circular loop 26, or the smaller transverse axis of an elongated end loop 27 need not be excessively large but must be sufficiently large to enable the inside of the loop to be engaged by a suitable instrument such as a puller or keeper, and a convenient guide is that such internal dimension should be approximately equal to or not less than twice the diameter of a strand 22, 23 of the tie member.

It will be appreciated that the lengths of the tie members are in no way restricted to the shapes of end loops as illustrated in FIG. 1A, 1B, 1C and that any arrangement of end loops can be provided with any length of tie member.

It is very desirable that the external surface of the tie member should be smooth, free of roughness in order to reduce the risk of damage to the spinal cord when a tie member is inserted in, adjusted in, and withdrawn from a segment of the spinal column.

It is believed that the advantages of a tie member embodying the present invention can best be understood by a description of one manner in which such tie member can be used in the treatment of spinal disorders, particularly since particular instruments enable a tie member to be used safely, efficiently and easily. One manner of using a number of tie members will now be described with reference to FIGS. 2 to 15 of the accompanying drawings.

When it is desired to attach a link or frame to a number of segments of a spinal column, a tie member 30 of suitable length is selected and is held in a pair of forceps 31 as illustrated in FIG. 2 and one end portion of the tie member is bent as illustrated at 32. As will be noted from FIG. 2 the bent end portion is located at one end of a segment 33 of the spinal column and forceps 31 are located at the other end of that segment thereby effectively marking on the tie member 30 a length suitable to enable the tie member to be inserted through that segment 33, and a further bend is effected in the tie member 30 as illustrated at 34 in FIG. 3. The tie member 30 is then in a suitable shape to enable it to be readily threaded through the segment 33 as illustrated diagrammatically in FIG. 4 in which the tie member 30 is held manually as illustrated at 35. The projecting end loop 36 can now be engaged firstly to enable the tie member to be pulled through to a sufficient extent and secondly to keep the end portion of the tie member at a desired location.

The foregoing procedure is followed with other tie members until a desired number of tie members have been inserted through pre-selected segments of the spinal column. FIG. 5 illustrates diagrammatically the conditions that may then obtain. Two tie members 41, 42 have been inserted through opposite sides of a first segment 43 of a spinal column and two further tie members 44, 45 have been inserted through opposite sides of an adjacent segment 46. The two end loops 47, 48 of the tie member 41 are retained in a keeper 49. Similarly both the end loops of each of the other tie members 42, 44 and 45 are retained in a keeper 50, 51, 52 respectively.

One form of keeper 53 is illustrated in FIG. 6 and comprises a pair of box-jointed lever arms 54, 55 having conventional ring-shaped handles 56 and a locking ratchet mechanism 57; both of the operating arms 58, 59 have a substantially semi-circular recess 60, 61 and the ends of the arms, when the keeper is fully closed, do not abut one another but define a transverse recess 62. As may be more clearly seen in FIG. 8, one of the arms 58 carries a transversely extending pin 63 which is receivable in a transverse bore 64 in the other arm 59. The diameter of the pin 63 is suitably chosen in relation to the internal dimension of the end loop of a tie member 5 such that it can be readily received therein, and the width of the transverse recess 62 is similarly chosen in relation to the thickness of the strands of a tie member, such that two tie members can be satisfactorily retained in a keeper when fully closed. The lever handles 54, 55 can be plain as illustrated in FIG. 6 or can be angled at 65 as illustrated in FIG. 7.

A keeper as illustrated in FIGS. 6 to 8 can be used not only to retain two end loops of a tie member but can, of course, also be used to engage the leading, or if necessary the trailing end loop of a tie member to assist in its insertion and manipulation into a desired position. A plurality of keepers can be disposed at either side of a patient and extend away from an incision giving access to the spinal column. Whilst such keepers can be used, as will be subsequently described, for twisting the end portions of tie members, their use is not essential solely for the purpose of retaining the end loops of a tie member and alternatively, a weighted flexible hook keeper can be used and indeed may be desirable when a large number of tie members are being used. Such an alternative tie member keeper is illustrated in Fig. 9 and comprises a hook-shaped member 66 which can be engaged in the end loops of a tie member and which is connected by a flexible member 67 leading to a weight 68 which can be allowed to hang at one side of the operating table. Yet again a tie member can be retained by threading a tape of suitable material such as nylon through its end loops, securing the ends of the tape in forceps, and allowing the tape to hang at one side of the wound.

A further instrument suitable for pulling in a tie member is illustrated at 69 in FIG. 10 and comprises a shaft having a hook 70 at one end and a T-shaped handle 71 at the other. Moreover, after a tie member has been pulled through and adjusted so that substantially equal lengths protrude from a segment, both the end loops can be engaged by the hook 70 of the instrument 69, and the member pulled up therewith so as to be hard against the medullary surface of the segment and the protruding portions of the tie member contoured manually against the dorsal surface of the segment in order to avoid the tie member being accidentally pushed back into the segment and engaging the spinal column therein. This procedure can be carried out before the end loops of the tie member are retained by engagement with a keeper 53 or a weighted flexible hook member or a tape.

After all the desired tie members have been inserted through the selected segments of the spinal column, the end loops of each of the tie members are separated from one another and one end region of each tie member is threaded through a link or frame member 80 which is then placed to embrace the rear parts of the selected segments of the spinal column, whereupon the two end loops of each of the tie members are brought together and retained in a keeper. The conditions then obtaining are illustrated diagrammatically in FIG. 11. It is now required to twist together the two ends of each of the tie members and this can be conveniently effected by means of a twister 81, as illustrated in FIG. 12, which comprises a shaft 82 having at one end a keeper engaging member 83 and, at its other end a crank handle 84. A manually engagable bearing sleeve 85 is disposed on the shaft 82 adjacent the handle 84. The keeper engaging member 83 has a T-shaped forwardly tapering groove 86 which is shaped and dimensioned appropriately to receive part of a keeper. The shaft 82 is cranked as at 87 such that the axis of the portion of the shaft adjacent the handle 84 and within the sleeve 85 is substantially coaxial with a keeper 53. The twister 81 is engaged on a keeper 53 by a sliding action; the tapering T-shaped groove 8 is wide enough at its rear end to receive the arms 58, 59 of the keeper 53 whereupon the twister 81 is pulled rearwardly relatively to the keeper 53 so that by a sliding action the arms 58, 59 move along the T-shaped groove 86 to project from the forward narrow end of the T-shaped groove whilst the lever arms 54, 55 are effectively clamped in the side parts of the T-shaped groove 86 as illustrated in FIG. 13. After the twister 81 is engaged on a keeper 53, the bearing sleeve 85 is held manually and the crank handle 84 is rotated in order to twist together the ends of a tie member retained in the keeper. The twister 81 is then disengaged from that keeper 53 by sliding the twister forwardly relatively to the keeper and the keeper thereafter is opened and disengaged from the end loops of that tie member; the same procedure is followed with each of the other tie members so that the selected segments of the spinal column are clamped to the frame or link member 80. conditions then obtaining are illustrated diagrammatically in FIG. 14 in which the segment 43 is shown as being clamped to the frame or link 80 by tie members 41, 42 whose end portions are twisted together as illustrated at 88, 89, and can be disposed as desired.

When at a subsequent stage in treatment it is desired to release a segment of the spinal column from the link or frame, access is gained to the back of the spinal column and the twisted end regions of each of the tie members are located and engaged in a keeper which is then used to untwist the ends. This may conveniently be done by utilising a twister 81 as illustrated in FIGS. 12 and 13 and rotating the crank handle 84 in the opposite direction. After untwisting the end portions of each tie member can be separated as illustrated in FIG. 15 at 90 and 91 in respect of the tie member 41 and after release and removal of the link or frame 80 each of the tie members can be carefully shaped and gently withdrawn from a segment of the spinal column using, if necessary, one or more keepers 53, 54 and/or a hook shaped puller 69 and gently and carefully withdrawn from the segment concerned. Since, even when untwisted after having been previously twisted, the external surface of a tie member can still be smooth and free from roughness, its removal is greatly facilitated and the risk of damage to the spinal cord passing through that segment during withdrawal of the tie member can be obviated or at least substantially reduced.

It will be readily apparent that a tie member embodying the present invention possesses a number of advantages not least of which is a substantial reduction in the risk of damage to the spinal cord during removal, or indeed during insetion, or manipulation, of a tie member.

When compared with the use of a tie member in the form of a long length of wire, or of a continuous length of wire, a tie member which is of a known length is advantageous. With a range of lengths of tie members, it is possible to select a tie member of a length most suitable for a particular segment of a spinal column, virtually by direct comparison of the tie member with that segment. Moreover using a tie member of known length obviates a required length of wire having to be cut from a longer length prior to insertion, such cutting bring the attendant risk of damage by a shape edge of the wire. A tie member of known length, and which is therefore comparatively short as compared with a tie member of unspecified length, does not have an unnecessary redundant length which has to be trimmed away after insertion or which could establish a long lever arm projecting from the spinal column such as might be displaced accidentally during the application of the link or frame and causes the tie member to be pushed down onto the spinal cord.

The provision of the end loops enables the end regions of a tie member to be positively and securely held in a keeper or to be safely held by a tape. When a pair of rod members serve as part of the link or frame member and a tape is used to hold the end regions of each tie member, such tape need not be withdrawn from the end loops before such rods are applied to the spinal column as the rods can be slid through the loops formed by the tie members.

A tie member embodying the present invention and having a smooth external surface substantially free of roughness, especially by virtue of the end loops, does not have any shape end which could penetrate a surgeon's glove or a patient's tissue.

I claim:

1. A surgical tie member for insertion through a segment of a spinal column for clamping that segment to a link or frame member embracing that segment, said tie member comprising:
    an endless loop of wire which loop has been flattened to form two endless strands extending continuously without interruption from one end region to another end region;
    said strands extending substantially parallel to one another from one end region to the other end region;
    said strands being substantially contiguous with one another at least adjacent said end regions; and
    each strand running into the other strand in each end region and both strands defining an end loop in each end region and dimensioned to be inserted through a segment of spinal column and wherein the loops are coplanar wtih the strands and the strands are adapted to be bent about an axis transverse to the strands into a retained position for inserting through a segment of a spinal column, the loops being dimensioned for insertion through a segment of spinal column.

2. A tie member as set forth in claim 1, wherein the end loops at both end regions of the tie member are similar shapes.

3. A tie member as set forth in claim 1, wherein the end loops are differently shaped at opposite ends.

4. A tie member as set forth in claim 1, wherein at least one end loop is substantially circular.

5. A tie member as set forth in claim 1, wherein at least one end loop is elongated.

6. A tie member as set forth in claim 1, wherein at least one end loop has substantially parallel sides joined by a substantially circular end portion.

7. A tie member set forth in claim 1, wherein each end loop has a transverse internal dimension substantially equal to twice the diameter of a strand of the tie member.

8. A tie member as set forth in claim 1, wherein each end loop has transverse internal dimension not less than twice the diameter of a strand of the tie member.

9. A tie member as set forth in claim 1, wherein the length of the tie member is not less than 75 mm and not greater than 150 mm.

10. A tie member as set forth in claim 1, which tie member is made of stainless steel.

11. A surgical tie member for insertion through a segment of a spinal column for tieing that segment to members embracing that segment, said tie member comprising in combination:
    a one-piece, wire-like body including two endless strands extending longitudinally in side by side relationship and being made of material adapted to be bent about an axis transverse to the strands into a retained position for insertion through a segment of spinal column, and
    two loops respectively located on the opposite ends of the strands and being integral with and formed by the strands and being dimensioned to be inserted through a segment of spinal column, and
    wherein said strands are generally parallel and contiguous to each other and lie in the same plane as said loops.

12. The tie member defined in claim 11, wherein all external surfaces of the body including the strands and loops are smooth and free of any roughness and the body is made of stainless steel.

13. A surgical tie member for insertion through a segment of a spinal column for clamping that segment to a link or frame member embracing that segment, said tie member comprising:
    an endless loop of wire which loop has been flattened to form two endless strands extending continuously and without interruption from one end region to another end region;
    said strands extending substantially parallel to one another from one end region to the other end region;
    said strands being substantially contiguous with one another at least adjacent said end regions;
    each strand running into the other strand in each end region and both strands defining an end loop in each end region and dimensioned to be inserted through a segment of spinal column and wherein the loops are co-planar with the strands and the strands are adapted to be bent about an axis transverse to the strands into a retained position for inserting through a segment of a spinal column, the loops being dimensioned for insertion through a segment of spinal column; and
    wherein the loops and strands are made of stainless steel and all external surfaces thereof are smooth and free of any roughness.

* * * * *